United States Patent [19]

Kato et al.

[11] 4,346,406

[45] Aug. 24, 1982

[54] GRADATION PROCESSING METHOD FOR A RADIATION IMAGE RECORDING SYSTEM

[75] Inventors: Hisatoyo Kato; Masamitsu Ishida, both of Minami-ashigara, Japan

[73] Assignee: Fuji Photo Film Co., Ltd., Kanagawa, Japan

[21] Appl. No.: 168,799

[22] Filed: Jul. 11, 1980

[30] Foreign Application Priority Data

Jul. 11, 1979 [JP] Japan ................................. 54-87805

[51] Int. Cl.³ .............................................. H04N 5/30
[52] U.S. Cl. .................................. 358/110; 358/174; 358/160; 358/111
[58] Field of Search ............... 358/174, 110, 111, 112, 358/113, 160; 250/327.1, 337

[56] References Cited

U.S. PATENT DOCUMENTS 3,859,527  1/1975  Luckey ............................... 250/337

Primary Examiner—Michael A. Masinick
Attorney, Agent, or Firm—Gerald J. Ferguson, Jr.; Joseph J. Baker

[57] ABSTRACT

In a radiation image recording system using a stimulable phosphor in which a radiation image is once recorded and then read out by use of stimulating rays impinging thereupon, the gradation of the image is processed by setting the read out level of the read out system and by setting the gain of the read out system. Among the image signal read out from the stimulable phosphor, the maximum Smax, the minimum Smin and the average $\bar{S}$ are determined. When logSmax−logSmin is less than a predetermined value, Smin is made a standard input signal. When it is more than the predetermined value, $\bar{S}$ or (logSmax+logSmin)/2 is made a standard input signal. The standard input signal is read out as a predetermined level of a standard output signal. Further, the gain of amplification in the image read out system is controlled to be Δs/(logSmax−logSmin) in the former case, and is fixed in the latter case, where Δs is a reproduced signal region.

7 Claims, 10 Drawing Figures

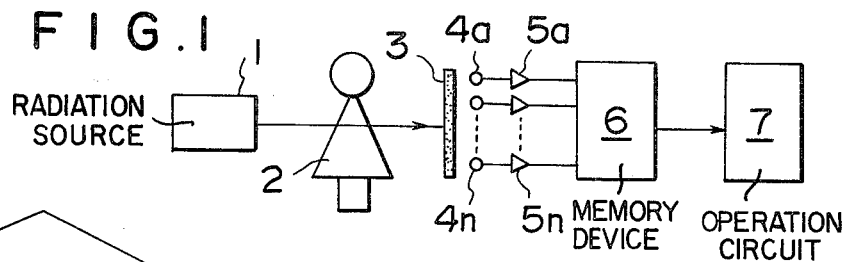
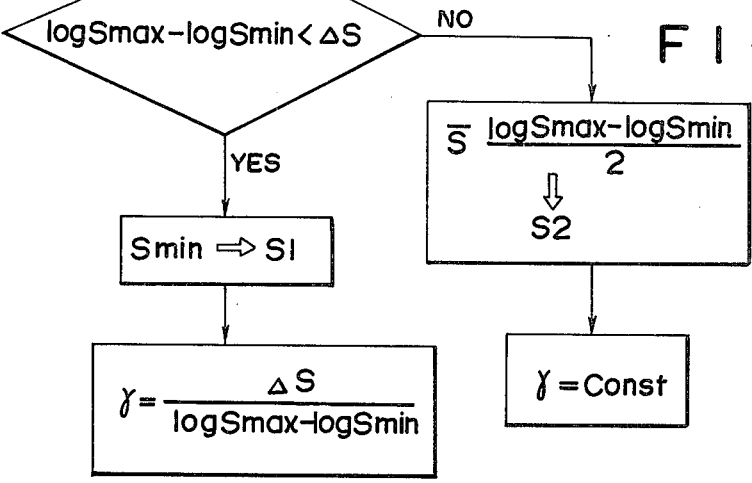
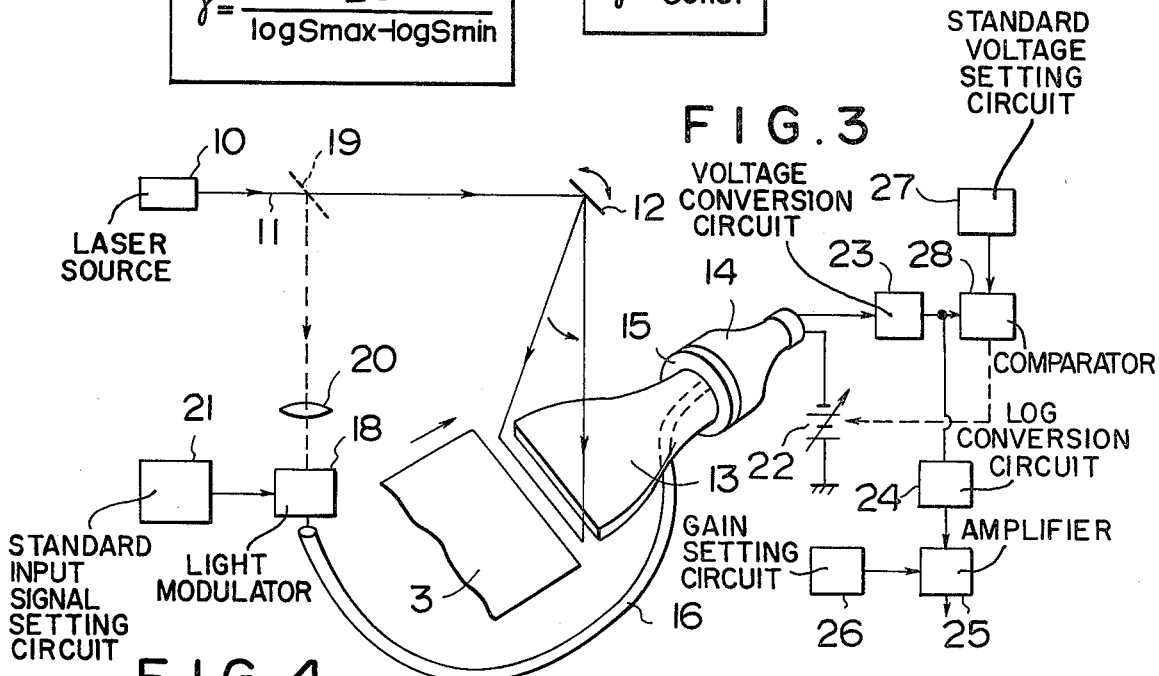
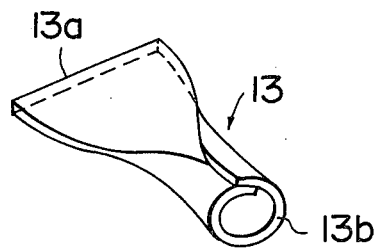
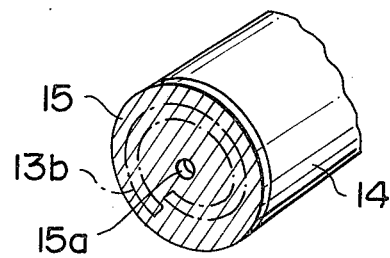

GRADATION PROCESSING METHOD FOR A RADIATION IMAGE RECORDING SYSTEM

BACKGROUND OF THE INVENTION

1. Field of the Invention

This invention relates to a radiation image information read out system for scanning a stimulable phosphor plate with a light beam of stimulating rays to cause the stimulable phosphor plate carrying radiation image information to emit light according to the radiation image information stored therein in the form of radiation energy, and more particularly to a method of gradation processing for the radiation image information read out system in which the gradation of the finally obtained image is controlled by controlling the output level and the gain of the read out system at the time of image information read out step.

2. Description of the Prior Art

A stimulable phosphor stores a part of the energy of a radiation when exposed to the radiation like X-rays, α-rays, β-rays, γ-rays and ultraviolet rays. Then, when the stimulable phosphor which has been exposed to the radiation is exposed to stimulating rays, light is emitted from the stimulable phosphor upon stimulation thereof according to the stored energy of the radiation.

As disclosed in U.S. Pat. No. 3,859,527, it has been known to use the stimulable phosphor for recording a radiation image. In more detail, the stimulable phosphor is first exposed to X-rays to memorize a radiation image therein, the stimulable phosphor is then scanned with stimulating rays to emit light according to the memorized image, the light emitted from the stimulable phosphor upon stimulation thereof is detected by a photodetector to obtain an image signal, and the image signal is used for controlling a laser beam for recording an image on a photosensitive film.

By use of this system, it is possible to obtain a radiation image useful for diagnosis. In order to obtain an image useful for diagnosis, the image should be reproduced into a desirable range of density. However, the image used for diagnosis has a very wide range of density in some cases like a mammograph or image of the head, and a comparatively narrow range of density in other cased like a plain image of the abdomen. Further, in case that a contrast medium or a lead protector is used, the image includes a portion of very low density and accordingly of very low level of the image signal. It is very difficult to record the image having such various types of density distribution in a proper density. Therefore, a proper gradation processing has relied upon the skill of the operator.

Further, the operator reads out the recorded image information and records the read out information once in a magnetic tape and determines the gradation processing condition by analyzing the image characteristics by use of a histogram and the like. In this case, a recording means having a large capacitor is necessitated and the structure of the recording apparatus becomes complicated and further it takes a long time for reproduction of the image.

SUMMARY OF THE INVENTION

The object of the present invention is to provide a gradation processing method in which the gradation process is simply, at a high speed performed without a help of an operator and by which a radiation image having a stable reproduction density and high diagnostic efficiency and accuracy are obtained.

The above object is accomplished by detecting the maximum value Smax, the minimum value Smin and the average value $\bar{S}$ from the image signal measured at the time of recording the radiation image, classifying the process based on the difference of (log Smax − log Smin), when the difference is below a predetermined value setting the level of the photodetector so that the Smin will be the first standard output signal S1 and amplifying the image signal with a gain γ of $$\gamma = \frac{\Delta s}{\log S\max - \log S\min}$$

where the signal region corresponding to the reproduction density region $\Delta D$ is $\Delta s$, and when the difference is above the predetermined value setting the level of the photodetector so that the $\bar{S}$ or (log Smax + log Smin)/2 will be the second standard output signal S2 and amplifying the image signal with a fixed gain determined to cover a wide range of light emission.

In accordance with the present invention, the level and the gain of the photodetector or the gain of an amplifier for amplifying the output signal of the photodetector is controlled at the time of radiation image read out step, whereby the contrast of the reproduced image is controlled. Accordingly, the gradation processing can be made simply at a high speed.

As the stimulable phosphor which is desired to emit light having a wavelength within the range of 300 to 500 nm. For example, rare earth activated alkaline earth metal fluorohalide phosphor is preferred. One example of this phosphor is, as shown in Japanese unexamined Patent Publication No. 55(1980)-12143, a phosphor represented by the formula $(Ba_{1-x-y},Mg_x,Ca_y)FX:aEu^{2+}$ wherein X is at least one of Cl and Br, x and y are numbers satisfying $0 < x+y \leq 0.6$ and $xy \neq 0$, and a is a number satisfying $10^{-6} \leq a \leq 5 \times 10^{-2}$. Another example of this phosphor is, as shown in Japanese unexamined Patent Publication No. 55(1980)-12145, a phosphor represented by the formula $(Ba_{1-x},M^{II}_x)FX:yA$ wherein $M^{II}$ is at least one of Mg, Ca, Sr, Zn and Cd, X is at least one of Cl, Br and I, A is at least one of Eu, Tb, Ce, Tm, Dy, Pr, Ho, Nd, Yb and Er, x is a number satisfying $0 \leq x \leq 0.6$, and y is a number satisfying $0 \leq y \leq 0.2$. Further, as the stimulable phosphor to be used in this invention can be used ZnS-Cu,Pb; BaO.xAl$_2$O$_3$:Eu wherein $0.8 \leq x \leq 10$; and $M^{II}O.xSiO_2$:A wherein $M^{II}$ is Mg, Ca, Sr, Zn, Cd or Ba, A is Ce, Tb, Eu, Tm, Pb, Tl, Bi or Mn, and x is a number satisfying $0.5 \leq x \leq 2.5$, as shown in Japanese unexamined Patent Publication No. 55(1980)-12142. Furthermore, as the stimulable phosphor can be used LnOX:xA wherein Ln is at least one of La, Y, Gd and Lu, X is at least one of Cl and Br, A is at least one of Ce and Tb, x is a number satisfying $0 < x < 0.1$, as shown in Japanese unexamined Patent Publication No. 55(1980)-12144. Among the above numerated phosphors, the rare earth activated alkaline earth metal fluorohalide phosphor is the most preferable, among which barium fluorohalides are the most preferable in view of the high intensity of emission of light.

Further, it is desirable to color the phosphor layer of the stimulable phosphor plate made of the above phosphor by use of pigments or dyes to improve the sharpness of the image obtained thereby as disclosed in Japanese Patent Application No. 54(1979)-71604.

As the stimulating rays for stimulating the stimulable phosphor to cause the phosphor to emit light is used a laser beam having high directivity. As the light source for the laser beam is preferred a laser source capable of emitting light having a wavelength within the range of 500 to 800 nm, preferably 600 to 700 nm. For example, a He-Ne laser (633 nm) and a Kr laser (647 nm) can be used. Other light sources can be used if combined with a filter which cuts out the light of the wavelength of less than 500 nm and more than 800 nm.

BRIEF DESCRIPTION OF THE DRAWING

FIG. 1 is a schematic view showing the radiation image recording system in which the gradation processing method of this invention is employed, FIG. 2 is a flow chart of the gradation processing method of this invention, FIG. 3 is a perspective view of a radiation image information read out system, FIG. 4 is a perspective view of a light guiding sheet employed in an embodiment of the present invention, FIG. 5 is a partial perspective view showing the light receiving face of a photomultiplier used in an embodiment of the present invention.

DESCRIPTION OF THE PREFERRED EMBODIMENTS

Figure 6:
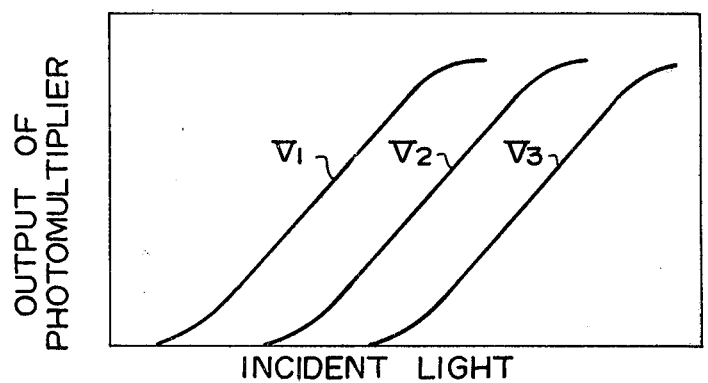
FIG. 6 is a graph showing the output characteristic of a photomultiplier.

Now the present invention will be described in detail with reference to the drawing.

Referring to FIG. 1 showing a radiation image recording system, a radiation source 1 emits a radiation like X-rays which transmits through an object like a human body and impinges upon a stimulable phosphor plate 3 located therebehind. The stimulable phosphor plate 3 stores a part of the energy of the radiation impinging thereupon.

The stimulable phosphor plate 3 has a size of, for instance, 30 cm×30 cm and is composed of a substrate as of cellulose triacetate and a stimulable phosphor layer as of BaFBr:Eu phosphor having a mean grain size of 10$\mu$ applied thereon by use of nitrocellulose and having a thickness of 200$\mu$ dried.

The stimulable phosphor plate emits light even when it is exposed to the radiation at the time of recording the radiation image. Then, a number of photodiodes 4a to 4n are located behind the stimulable phosphor plate 3 to read out the light emitted therefrom upon exposure to the radiation. The output of the photodiodes 4a to 4n is connected to a number of amplifiers 5a to 5n to be amplified thereby and is then memorized in a memory device 6.

The data memorized in the memory device 6 are read out and operated through an operation circuit 7. Thus, the maximum value Smax, the minimum value Smin and the average value $\overline{S}$ are obtained thereby.

Further, it is possible to provide another phosphor plate in front of the photodiodes 4a to 4n to measure the light emitted therefrom when the phosphor plate is exposed to the radiation transmitted through the stimulable phosphor plate 3.

FIG. 2 shows a flow chart of the method of the present invention. In said operation circuit 7, it is determined if the formula of (log Smax−log Smin)<$\Delta$s is satisfied or not. $\Delta$s shows the reproduced image signal region which is finally converted to the density region of the photographic film. For instance, when the reproduced image region is made within the range of optical density 0.2 to 2.2 and set at 2.0, the signal region reproduced corresponding thereto is $\Delta$s.

If the difference as defined in said formula is less than $\Delta$s, the level of the read out system is set so that the Smin becomes the first standard output signal S1. In this case, the gain of the read out system is set so that the amplification rate $\gamma$ is made $$\frac{\Delta s}{\log Smax - \log Smin}.$$

If the difference as defined in said formula is more than $\Delta$s, the level of the read out system is set so that the S or (log Smax+log Smin)/2 becomes the second standard output signal S2. In this case, the gain $\gamma$ is maintained at a fixed value in amplification.

FIG. 3 shows an embodiment of the image read out system in which the present invention is employed. A laser source 10 which emits a laser beam having a wavelength within the range of 600 to 700 nm is used. The laser beam 11 emitted from the laser source 10 is deflected in one direction by a light deflector 12 like a galvanometer mirror. The stimulating rays or the laser beam deflected by the light deflector 12 impinge upon a stimulable phosphor plate 3 at a substantially right angle. The stimulable phosphor plate 3 moves in the direction indicated by an arrow and whereby the stimulable phosphor plate 3 is scanned two-dimensionally.

Possibly close to the primary scanning line of the stimulable phosphor plate 3 is located a light guiding sheet 13. The light guiding sheet 13 has a flat end 13a to be located close to the primary scanning line on the stimulable phosphor plate 3. The opposite end face 13b of the light guiding sheet 13 is shaped into a ring-shaped form to be put into contact with the light receiving face of the photodetector 14. As the light guiding sheet is used one as described in detail in Japanese Patent Application No. 54(1979)-87807.

The number of the light guiding sheets 13 may not be one, but two light guiding sheets may be located symmetrically with respect to the primary scanning line on the stimulable phosphor plate 3. Further, one or more light guiding sheets may be located above the stimulable phosphor plate and another one or more light guiding sheets may be located below the stimulable phosphor plate 3.

The light collected by the light guiding sheet 13 is received by a photodetector 14 like a photomultiplier provided in contact with the light output face 13b of the light guiding sheet 13. The photodetector 14 has a circular light receiving face to be contacted with the light output face of the light guiding sheet 13. The photomultiplier 14 used has a spectroscopic sensitivity of S-11 type.

As shown in FIG. 5, on the light receiving face of the photomultiplier 14 is attached a filter 15 which has transmittance of 80% for the emitted light of 400 nm and 0.1% or less for the light of 633 nm. The light output face 13b of the light guiding sheet 13 is put into contact with the filter 15, whereby only the light having a wavelength within the range of 300 to 500 nm is measured by the photomultiplier 14.

The filter 15 is provided with a hole 15a at the center thereof at which the light output end of an optical fiber bundle 16 is contacted. Therefore, the light transmitted through the optical fiber bundle 16 directly enters the photomultiplier 14.

The optical fiber bundle 16 is located at such a position that the light receiving end thereof receives light modulated by a light modulator 18 like an A/O modulator.

The laser beam emitted from the laser source 10 is reflected toward the A/O modulator 18 through a lens 20 by a mirror 19 which is inserted into the optical path of the laser beam in the step of setting the gradation. The mirror 19 may be replaced by a beam splitter like a semi-transparent mirror which reflects a part of the laser beam toward the A/O modulator 18.

The A/O modulator 18 controls the amount of light of the laser beam according to the standard signal from a standard input signal setting circuit 21. The A/O modulator 18 may be replaced by a rotatable disc having a continuously changing density which controls the amount of light passing therethrough by the angle of rotation thereof, or by a knife edge which is movable to control the amount of light.

The photomultiplier 14 is driven with a high voltage by a power source 22 so that, for example, the voltage is controlled within the range of $-500$ V to $-1000$ V. That is, as shown in FIG. 6, by changing the voltage from V1 to V3, the output level of the photomultiplier 14 is changed.

The output current of the photomultiplier 14 is sent to a log conversion circuit 24 after converted to a voltage value by the voltage conversion circuit 23. Then, after converted to a log value by the log conversion circuit 24, the output signal is sent to an amplifier 25. The gain of the amplifier 25 is controlled by the signal from a gain setting circuit 26.

When the gradation is to be set in the read out system, the output voltage of the photomultiplier 14 and the standard output signal from the standard voltage setting circuit 27 namely S1 or S2 are compared by a comparator 28 and the high voltage source 22 of the photomultiplier 14 is controlled so that both become equal to each other.

Now, the operation of the radiation image information read out system will be described in detail.

When the radiation image information is read out from the stimulable phosphor plate 3, the mirror 19 is at first put into the optical path of the laser beam from the laser source 10 to reflect the laser beam to the A/O modulator 18. The A/O modulator 18 modulates the intensity of the laser beam according to the standard input signal from the standard signal setting circuit 21.

When the difference of (log Smax−log Smin) is less than a predetermined value Δs, the output level of the photomultiplier 14 is set so that the Smin becomes equal to the first standard output signal S1. In case that the standard output signal S1 is made equal to Smin (S1=Smin), the A/O modulator 18 is controlled by the signal Smin. The modulated laser beam is transmitted to the photomultiplier 14 through the optical fiber bundle 14. The output signal of the photomultiplier 14 is converted to a voltage value by the voltage conversion circuit 23 and sent to the comparator 28.

Figure 7:
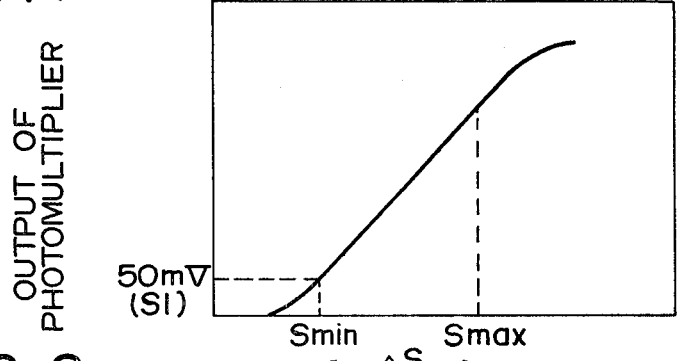
FIGS. 7 and 8 are graphs showing the output characteristic of the photomultiplier used for setting the output level thereof.

At the comparator 28, the output of the photomultiplier 14 and the first standard output signal S1 are compared and the high voltage source 22 is controlled to make them equal to each other. If the first standard output signal S1 is 50 mV here, the output level of the photomultiplier 14 is set as shown in FIG. 7.

Then, simultaneously with the level setting operation, a gain γ calculated by the formula $$\gamma = \frac{\Delta s}{\log S\max - \log S\min}$$

is input into the amplifier 25 from the gain setting circuit 26.

After the level and the gain are set as above, the mirror 10 is removed from the optical path of the laser beam and the light deflector 12 scans the stimulable phosphor plate 3 with the laser beam. The light emitted from the stimulable phosphor plate 3 upon scanning with the laser beam is transmitted to the photomultiplier 14 through the light guiding sheet 13.

Figure 9:
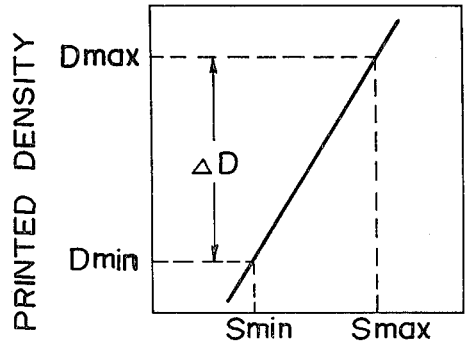
FIGS. 9 and 10 are graphs showing the density of the final image with respect to the level of the image signal used for setting the gain $\gamma$ of the image information read out system.

In this case, the gradation processing is conducted as shown in FIG. 9 and the contrast of the image is improved.

Figure 8:
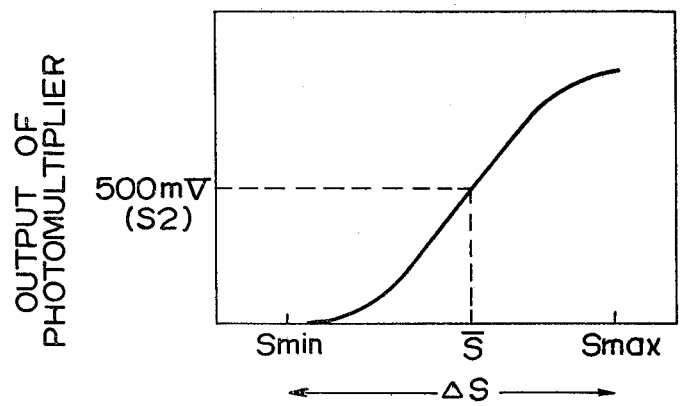

On the other hand, when the difference of (log Smax−log Smin) is more than Δs, namely, the transmittance of the radiation with respect to the image is distributed over a wide range, $\overline{S}$ or (log Smax+log Smin)/2 is used as the standard input signal, and the A/O modulator 18 is controlled thereby. Thus, when 500 mV is selected as the second standard output signal S2, the level is set so that the output voltage of the photomultiplier 14 becomes 500 mV as shown in FIG. 8.

Figure 10:
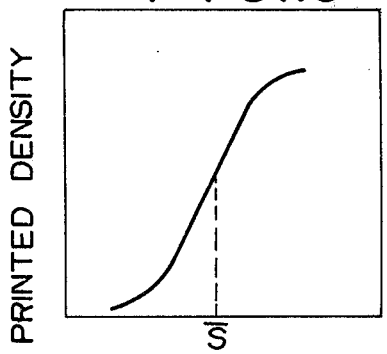

Simultaneously with the level setting, the gain γ of the amplifier 25 is set at a predetermined value. Therefore, the gradation as shown in FIG. 10 is performed.

By the gradation processing as mentioned above, a radiation image having any reproduced signal region was able to be reproduced into a proper density region. For instance, when Smin represented the extreme portion where the object was protected by a lead protector, the signal region to be reproduced becomes too large. Therefore, in such a case the level setting is performed by use of $\overline{S}$ or (log Smax+log Smin)/2, which prevented the increase of whole the image density. Further, in case of the object which provides a very small difference in absorption of radiation, the image was made legible by raising the gain. Further, when Smax represented a part outside the object and the reproduced region became too large, the level setting in accordance with this invention prevented the photomultiplier 14 from being degraded by the light of high intensity emitted from the part outside the object.

It should be understood that the present invention can be embodied in various types other than the above described embodiments. For instance, the characteristics as shown in FIG. 6 may be calibrated in detail in advance for the standard input signal represented by the abscissa so that the desirable high voltage of the power source for the photomultiplier required for obtaining a desired output level may be read out from the calibration and the dial of the high voltage power source may be operated to set the voltage properly.

We claim:

1. In a radiation image recording system including a radiation image information read out system having an amplification gain for scanning a stimulable phosphor plate with a light beam of stimulating rays to cause the stimulable phosphor plate carrying radiation image information to emit light according to the radiation image information stored therein in the form of radiation energy and detecting the emitted light to read out the radiation image information, a method of gradation processing comprising photoelectrically detecting the light emitted from the stimulable phosphor plate, determining the maximum value Smax, the minimum value Smin and the average value $\overline{S}$ among the image signal obtained by detecting the emitted light, setting the read out level of the radiation image information read out system so that the minimum signal level Smin is made a standard input signal when the difference of log Smax−log Smin is less than a predetermined value and a signal level other than the minimum signal level Smin is made a standard input signal when said difference is not less than said predetermined value and that said standard input signal is read out as a predetermined level of a standard output signal, controlling the amplification gain of the image information read out system to $\Delta s/(\log S_{max} - \log S_{min})$ where $\Delta s$ is a reproduced signal region in said former case, and fixing the amplification gain at a constant value in said latter case.

2. A method of gradation processing as defined in claim 1 wherein said predetermined value is said $\Delta s$.

3. A method of gradation processing as defined in claim 1 wherein said signal level other than the minimum signal level Smin is the average signal level $\overline{S}$.

4. A method of gradation processing as defined in claim 1 where said signal level other than the minimum signal level Smin is (log Smax+log Smin)/2.

5. In a radiation image recording system including a radiation image information read out system having an amplification gain for scanning a stimulable phosphor plate with a light beam of stimulating rays to cause the stimulable phosphor plate carrying radiation image information to emit light according to the radiation image information stored therein in the form of radiation energy and detecting the emitted light to read out the radiation image information, a method of gradation processing comprising photoelectrically detecting the light emitted from another phosphor plate located in the vicinity of the stimulable phosphor plate at the time of exposure of the stimulable phosphor plate to the radiation, determining the maximum value Smax, the minimum value Smin and the average value $\overline{S}$ among the image signal obtained by detecting the emitted light, setting the read out level of the radiation image information read out system so that the minimum signal level Smin is made a standard input signal when the difference of log Smax−log Smin is less than a predetermined value and a signal level other than the minimum signal level Smin is made a standard input signal when said difference is not less than said predetermined value and that said standard input signal is read out as a predetermined level of a standard output signal, controlling the amplification gain of the image information read out system to $\Delta s/(\log S_{max} - \log S_{min})$ where $\Delta s$ is a reproduced signal region in said former case, and fixing the amplification gain at a constant value in said latter case.

6. A method of gradation processing as defined in claim 5 wherein said signal level other than the minimum signal level Smin is the average signal level $\overline{S}$.

7. A method of gradation processing as defined in claim 5 where said signal level other than the minimum signal level Smin is (log Smax+log Smin)/2.

* * * * *